United States Patent [19]
Ayer et al.

[11] Patent Number: 5,707,663
[45] Date of Patent: Jan. 13, 1998

[54] SUSTAINED ANTIEPILEPTIC THERAPY

[75] Inventors: Atul Devatt Ayer, Palo Alto; Richard L.-C. Yieh, Millbrae; Brenda J. Pollock, Cupertino; Patrick S.-L. Wong, Palo Alto, all of Calif.

[73] Assignee: Alza Corporation, Palo Alto, Calif.

[21] Appl. No.: 442,425

[22] Filed: May 16, 1995

Related U.S. Application Data

[62] Division of Ser. No. 69,069, May 28, 1993.

[51] Int. Cl.$^6$ ............................................. A61K 9/26
[52] U.S. Cl. ........................................ 424/473; 424/494
[58] Field of Search .................................. 424/473, 494, 424/469, 461, 462, 486, 488

[56] References Cited

U.S. PATENT DOCUMENTS

| | | | |
|---|---|---|---|
| 2,799,241 | 7/1957 | Wurster | 118/24 |
| 3,133,132 | 5/1964 | Loeb et al. | 264/49 |
| 3,173,876 | 3/1965 | Zobrist | 252/137 |
| 3,276,586 | 10/1966 | Rosaen | 210/90 |
| 3,541,005 | 11/1970 | Strathmann | 210/19 |
| 3,541,006 | 11/1970 | Bixler | 210/23 |
| 3,546,142 | 12/1970 | Michaels t al. | 260/2.1 |
| 3,598,122 | 8/1971 | Zaffaroni | 128/268 |
| 3,598,123 | 8/1971 | Zaffaroni | 128/268 |
| 3,845,770 | 11/1974 | Theeuwes et al. | 128/260 |
| 3,865,108 | 2/1975 | Hartop | 128/260 |
| 3,916,899 | 11/1975 | Theeuwes et al. | 128/260 |
| 4,002,173 | 1/1977 | Manning et al. | 128/296 |
| 4,063,064 | 12/1977 | Saunders et al. | 219/121 |
| 4,088,864 | 5/1978 | Theeuwes et al. | 219/121 |
| 4,160,020 | 7/1979 | Ayers et al. | 424/15 |
| 4,200,098 | 4/1980 | Ayer et al. | 128/260 |
| 4,207,893 | 6/1980 | Michaels | 128/260 |
| 4,327,725 | 5/1982 | Cortese et al. | 128/260 |
| 4,612,008 | 9/1986 | Wong et al. | 604/892 |
| 4,765,989 | 8/1988 | Wong et al. | 424/473 |
| 4,783,337 | 11/1988 | Wong et al. | 424/468 |
| 5,192,550 | 3/1993 | Edgren et al. | 424/473 |

FOREIGN PATENT DOCUMENTS

| | | |
|---|---|---|
| A0133110 | 2/1985 | European Pat. Off. . |
| A0430287 | 6/1991 | European Pat. Off. . |
| A0442012 | 8/1991 | European Pat. Off. . |
| A2140687 | 12/1984 | United Kingdom . |

OTHER PUBLICATIONS

Remington's Phar. Sci. 18th Ed., pp. 1676–1686, Longer and Robinson, "Sustained–Release Drug Delivery Systems".

Remington's Phar. Sci., 17th Ed. (1985), p. 1637, Porter, "Coating of Pharmaceutical Dosage Forms".

The Pharmacological Basis of Therapeutics, By Goodman & Gilman, 7th Ed., (1985) p. 7.

Handbook of Common Polymers by Scott, J. R. and Roff, W. J., 1971.

J. Am. Pharm. Assoc., vol. 49, pp. 82–84, (1960) Wurster, Dale E., Preparation of Compressed Tablet Granulations by the Air Suspension Technique II.

J. Am. Phar. Assoc., Sci. Ed., vol. 48, Air–Suspension Technique of Coating Drug Particles, by Wurster Dale E.

*Primary Examiner*—Edward J. Webman
*Attorney, Agent, or Firm*—Paul L. Sabatine; Michael J. Rafa; Christopher P. Rogers

[57] ABSTRACT

This invention pertains to a dosage form for the management of epilepsies wherein the dosage form comprises administering valproic acid or a valproic acid derivative at a continuous rate over an extended time.

2 Claims, 5 Drawing Sheets

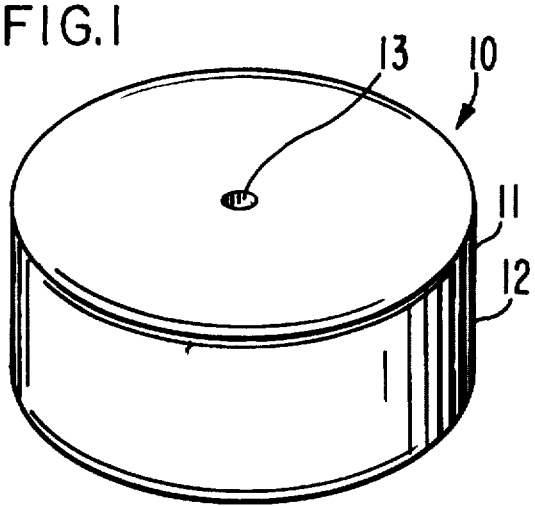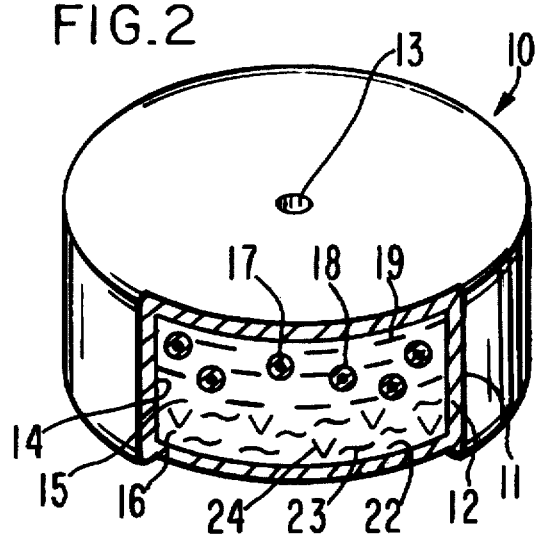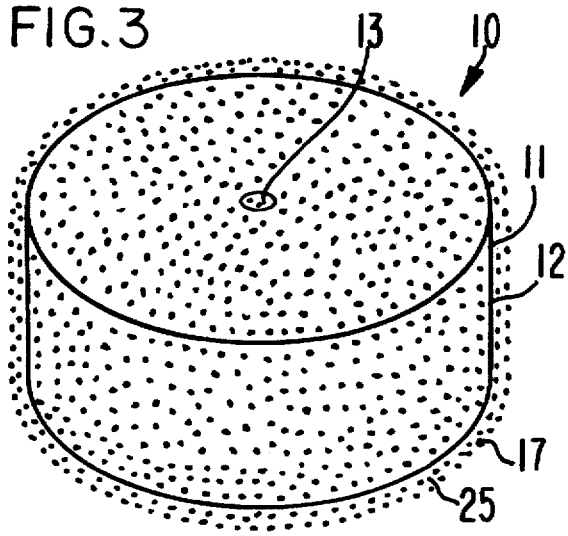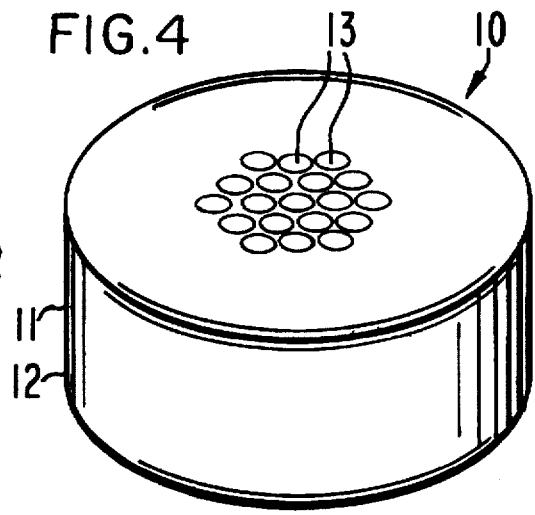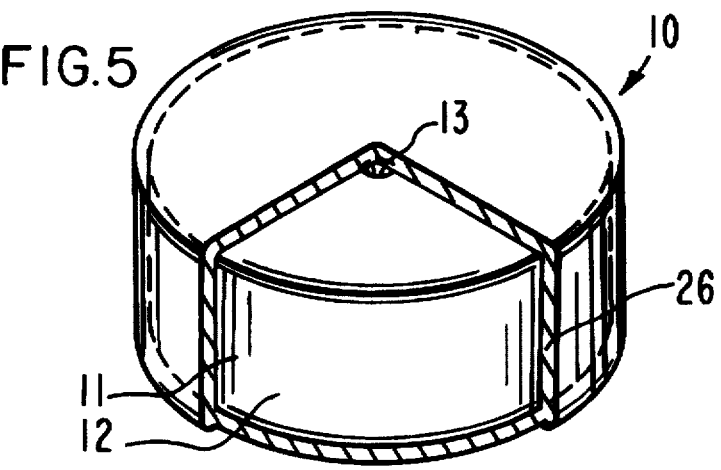

SUSTAINED ANTIEPILEPTIC THERAPY

This application is a division of application Ser. No. 08/069,069, filed May 28, 1993, and benefit of the filing date of said earlier filed application is claimed under 35 U.S.C. §120.

FIELD OF THE INVENTION

This invention pertains to a novel and to a nonobvious dosage form indicated for the management of epilepsies. The invention concerns also a composition comprising as antiepileptic drug and a carrier useful for manufacturing the dosage form and for dispensing the drug in an environment of use. The invention pertains further to a method for producing antiepileptic therapy in a patient in need of antiepileptic therapy.

BACKGROUND OF THE INVENTION

The term epilepsy is derived from a Greek word meaning a condition of being seized or overcome. The term epilepsy designates a group of central nervous system disorders having in common the occurrence of sudden and transitory episodes of abnormal behavioral symptoms of motor sensory, autonomic or psychic origin. Epilepsies have a definite onset and ending, and they usually are of short duration. Epilepsies are classified generally into two groups including generalized and partial, based on the type of seizures. Generalized seizures may involve a loss consciousness or convulsive movements, including tonic-clonic, myoclonic, tonic or clonic, and myoclonic astatic epilepsy. Partial seizures are divided into three subgroups including simple, complex, and secondarily generalized seizures.

Antiepileptic drugs are available for treating epilepsies. For example, valproic acid and its pharmaceutically acceptable salts are useful for treating epileptic phenomena. This drug is effective for its intended therapy; however, there are shortcomings associated with this drug. For instance, the antiepileptic drug valproic salt is extremely hygroscopic and liquifies very rapidly and it is sticky. The drug exhibits a short-half life that can lead to fluctuations in blood antiepileptic drug levels. These properties can interfere with the manufacture and release of the drug from a dosage form, and these shortcomings are serious drawbacks in the management of epilepsies.

Prior to this invention, the prior art administered an antiepileptic drug in a conventional dosage form like a tablet, or a capsule at repetitive dosing intervals. The prior art mode of therapy leads to a drug concentration in the blood during the dosing interval, and then a decrease in drug concentrations as a result of drug absorption, distribution, metabolism and elimination. The concentration difference in dosing intervals is related to the presence and to the absence of administered drug, which is a major disadvantage associated with conventional dosage forms. Conventional dosage forms and their mode of operation are discussed in Remington's *Pharmaceutical Sciences*, 18th Edition, pages 1676 to 1686 (1990), Mack Publishing Co.; *The Pharmacological Basis of Therapeutics*, 7th Edition, page 7, (1985) published by Macmillian Publishing Co.; Biopharmaceutics and Clinical Pharmacokinetics, 3rd Edition, pages 1 to 28, (1984), Published by Lea & Febiger, Philadelphia, Penn.; and in U.S. Pat. Nos. 3,598,122 and 3,598,123 both issued to Zaffaroni.

The above presentation dictates of the critical need for a dosage form that overcomes the shortcomings of conventional dosage forms, including tablets, capsules, elixirs and suspensions. These conventional dosage forms produce the peaks and valleys patterns discussed above, and they do not provide for dosage-regulated drug therapy over an extended period of time. The drug is dosed by the prior art twice or trice a day, which does not lead to controlled and sustained therapy. This prior art pattern of drug administration speaks of the need for a dosage form that can administer the drug in a rate-controlled pattern over an extended time to provide constant therapy and thereby eliminate the need for multiple dosing of the drug.

The prior art provided controlled-release dosage forms that can administer a drug continuously over time for controlled-rate therapy, as in, for example, in U.S. Pat. No. 4,327,725 issued to Cortese and Theeuwes and in U.S. Pat. Nos. 4,612,008; 4,765,989; and 4,783,337 issued to Wong, Barclay, Deters, and Theeuwes. The dosage forms disclosed in these patents provided a controlled rate of drug delivery over an extended time to provide constant drug therapy and thereby eliminate the need for multiple dosing of the drug. These dosage forms can deliver many drugs for their therapy, but there are certain drugs that are not readily manufactured and delivered from dosage forms. For example, sodium valproate because of its hygroscopic and tacky nature does not lend itself for providing a dosage form for controlled extended delivery since its properties hinder its manufacture into the dosage form and restrict its regulated delivery from such a dosage form.

It is immediately apparent, in the light of the above presentation, that an urgent need exists for a dosage form endowed with controlled-release delivery for administering valproic acid and its derivatives for antiepileptic valproic therapy. The need exists for this dosage form for delivering antiepileptic valproic acid in a controlled sustained dose in a therapeutic drug range and simultaneously provide extended therapy. It will be appreciated by those versed in the dispensing antiepileptic drug art, that to provide a dosage form that can administer an antiepileptic valproic drug in a controlled-rate dose over time, it would be seen as major advancement in the therapy of the epilepsies.

OBJECTS OF THE INVENTION

Accordingly, in view of the above presentation, it is an immediate object of this invention to provide a dosage form for delivering valproic acid and its derivatives that overcomes the shortcomings known to the prior art, and which dosage form can be manufactured by standard techniques.

Another object of the present invention is to provide a dosage form for the controlled delivery of valproic acid and its salts for maintaining an antiepileptic drug blood level in a therapeutic range over an extended time period.

Another object of the present invention is to provide a dosage form comprising means for stabilizing a hygroscopic antiepileptic drug contained in the dosage form.

Another object of the present invention is to provide a moisture-stable antiepileptic drug formulation and to the manufacture of the formulation into a dosage form.

Another object of the present invention is to provide a moisture-stable antiepileptic drug comprising a coating surrounding a hygroscopic antiepileptic drug particle that can be dispensed from a dosage form over an extended period of time.

Another object of the present invention is to provide a sustained-release dosage form that delivers an antiepileptic drug at a controlled-sustained rate for minimizing drug plasma fluctuations thereby providing antiepileptic drug in acute and chronic therapy.

Another object of the present invention is to provide a dosage form manufactured as an osmotic dosage form for the controlled delivery of antiepileptic valproic drug to a patient in need of antiepileptic valproic therapy.

Another object of the invention is to provide a method for treating a human being suffering from epilepsy, which method comprises administering to said human a dosage form containing an essentially moisture-stable antiepileptic drug.

Another object of this invention is to provide an improvement in a dosage form for administering a microencapsulated hygroscopic drug wherein the improvement comprises micro-encapsulating the hygroscopic drug with a water soluble polymer for substantially shielding the drug from a moisture environment.

Another object of the present invention is to provide a dosage form comprising microencapsulated drug granules that gradually release the drug resulting in a controlled and sustained release of the drug for improved plasma levels over a prolonged period of time up to thirty hours.

Another object of the present invention is to provide a dosage form for orally, buccally, or sublingually administering an antiepileptic drug surrounded with a polymer shield that imparts moisture-resistance to the antiepileptic drug.

Another object of the present invention is to provide a compressed composition comprising an encapsulated antiepileptic drug, which compressed composition essentially does not fracture during coating of the compressed composition with a composition comprising a semipermeable polymer.

Another object of the present invention is to provide a dosage form manufactured as an osmotic dosage form characterized by the ability to deliver an antiepileptic drug over a therapeutic range of one milligram to seven hundred and fifty milligrams over a period of from thirty minutes to thirty hours at a predetermined pattern to a biological recipient over time.

Another object of the present invention is to provide a dosage form that increases patient compliance by providing a dosage form that requires fewer doses by minimizing a missed dose of a prescribed drug for providing therapeutic efficiency for better health.

Other objects, features, aspects, and advantages of the invention will be more apparent to those versed in the antiepileptic drug dispensing art from the following detailed specification taken in conjunction with the drawing figures and the accompanying claims.

BRIEF DESCRIPTION OF THE DRAWINGS

In the drawings, which are not drawn to scale, but are set forth to illustrate various embodiments of the invention, the drawing figures are as follows:

Drawing FIG. 1 is a view of a dosage form designed and adapted for delivering an antiepileptic drug to a patient in need of antiepileptic therapy;

Drawing FIG. 2 is an opened view of the dosage form of drawing FIG. 1 for illustrating the structure of the dosage form;

Drawing FIG. 3 is a view of a dosage form comprising an antiepileptic drug dose on the exterior surface of the dosage form for providing instant antiepileptic drug in a short period of time;

Drawing FIG. 4 depicts a dosage form that comprises a multiplicity of exit ports for delivering an antiepileptic drug from the dosage form;

Drawing FIG. 5 depicts a dosage form comprising an exterior interior coat;

Drawing

Drawing

Drawing

Drawing

In the drawing figures and in the specification, like parts in related figures are identified by like numbers. The terms appearing earlier in the specification, and in the description of the drawing figures, as well as embodiments thereof, are further described elsewhere in the disclosure.

DETAILED DESCRIPTION OF DRAWING FIGURES

Figure 6:
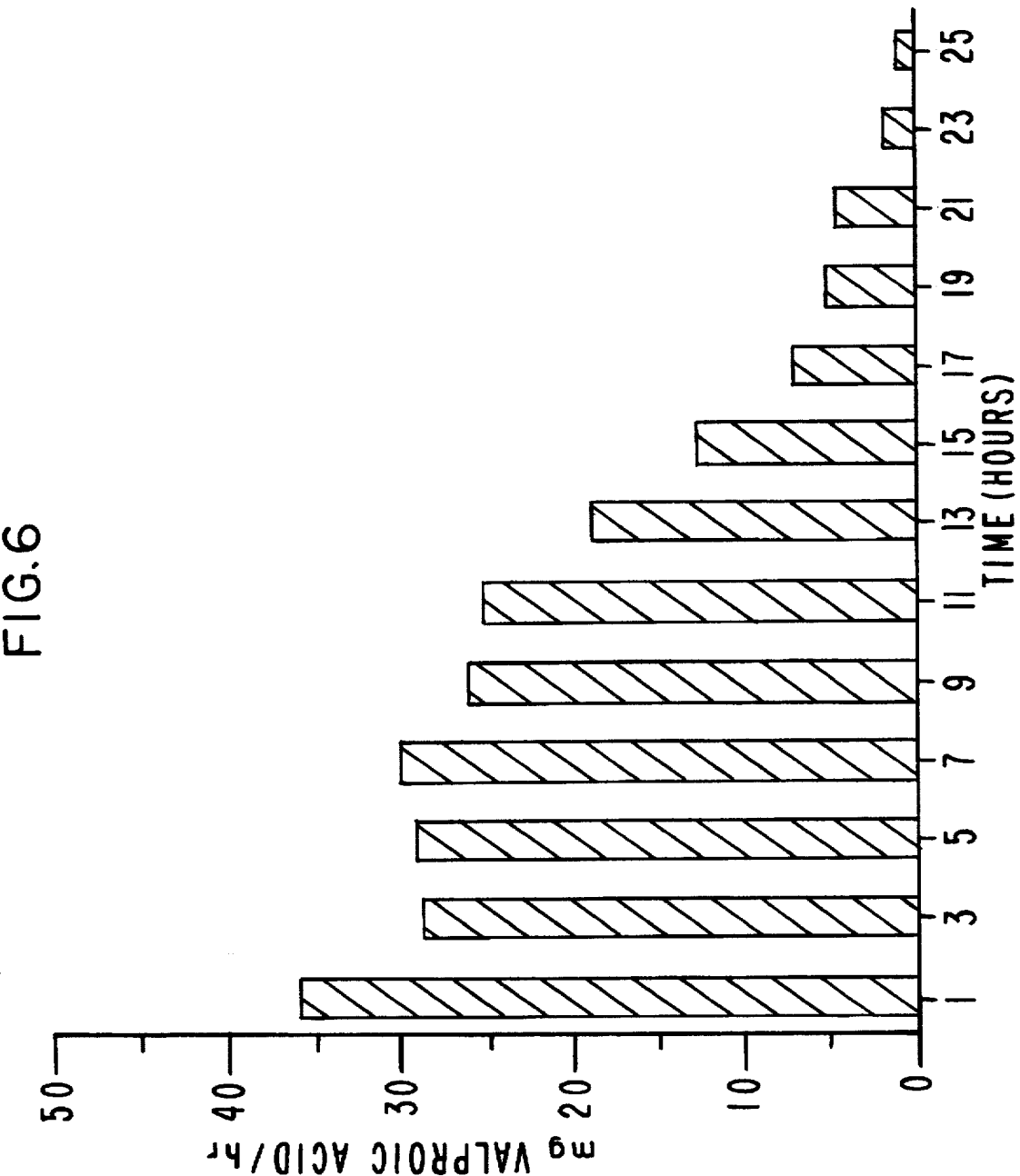
FIG. 6 depicts the release rate of valproic acid from a dosage form.

Turning now to the drawing figures in detail, which drawing figures are examples of the dosage forms provided by the invention, and which examples are not to be construed as limiting the invention, one example of the dosage form is illustrated in drawing FIG. 1, and it is designated by the numeral 10. In drawing FIG. 1, dosage form 10 comprises a body 11 comprising a wall 12 that surrounds and forms an internal compartment, not seen in drawing FIG. 1. Dosage form 10 further comprises at least one exit means 13, or more than one exit means 13 for connecting the interior of dosage form 10 with the exterior of dosage form 10.

Dosage form 10, as seen in drawing FIG. 2, depicts one presently preferred optional embodiment provided by this invention. Dosage form 10, as seen in drawing FIG. 2 comprises body 11, wall 12, and exit means 13. Wall 12 is opened at 14 for depicting internal compartment 15. Dosage form 10, as provided by this invention, can be manufactured for orally administering an antiepileptic drug to the gastrointestinal tract, and in additional embodiments, dosage form 10 can be sized and shaped for administering an antiepileptic drug by the sublingual and buccal routes. The sublingual and buccal routes can be used for quicker antiepileptic therapy, and they can be used when a smaller dose of antiepileptic drug is needed for therapy. The buccal and sublingual routes can be used as a by-pass of the first-pass of hepatic metabolism of the antiepileptic drug. The sublingual or buccal routes can be used for administering the first dose of the antiepileptic drug followed by permitting dosage form 10 to enter the stomach, intestine, and colon for continuous antiepileptic drug delivery.

Wall 12 of dosage form 10 comprises totally, or in part, a composition that is permeable to the passage of an exterior fluid present in the environment of use. Wall 12 is substantially impermeable to the passage of a drug and to other optional ingredients present in compartment 15. Wall 12 comprises a semipermeable composition that is substantially inert, that is, wall 12 maintains its physical and chemical integrity during the dispensing of the antiepileptic drug from dosage form 10. Wall 12 comprises nontoxic materials comprising a member selected from the group consisting of a cellulose ether, cellulose ester, cellulose ester ether, and cellulose. The cellulosic polymers have a degree of substitution, D.S., on the anhydroglucose unit, from greater than zero and up to 3 inclusive. By degree of substitution is meant the average number of hydroxyl groups present on the anhydroglucose unit comprising the cellulose polymer that are replaced by a substituting group. Representative materials include a polymer selected from the group consisting of cellulose acylate, cellulose diacylate, cellulose triacylate, cellulose acetate, cellulose diacetate, cellulose triacetate, mono, di, and tricellulose alkanylates, moni, di, and tricellulose aroylates, and mono, di, and tricellulose alkenylates. Exemplary polymers include cellulose acetate having a D.S. of an acetyl content up to 21%; cellulose acetate having an acetyl content up to 32 to 39.8%; cellulose acetate having a D.S. of 1 to 2 and an acetyl content of 21 to 35%; cellulose acetate having a D.S. of 2 to 3 and an acetyl content of 35 to 44.8%. More specific cellulosic polymers include cellulose propionate having a D.S. of 1.8 and a propyl content of 39.2 to 45 and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.,5 to 4.7%; cellulose triacylate having a D.S. of 2.9 to 3 such as cellulose triacetate, cellulose trivalerate, cellulose trilaurate, cellulose tripatmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentanoate, and coesters of cellulose such as cellulose acetate butyrate, cellulose acetate octanoate butyrate and cellulose acetate propionate.

Additional polymers possessing semipermeable properties for manufacturing wall 12 comprise acetaldehyde dimethyl cellulose acetate, cellulose acetate ethylcarbamate, cellulose acetate methylcarbamate, cellulose acetate dimethylaminocellulose acetate, semipermeable polyamides, semipermeable polyurethanes, semipermeable poly (sulfonated styrenes), semipermeable cross-linked selectively permeable polymers formed by the coprecipitation of a polyanion and polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; semipermeable lightly cross-linked polystyrene derivatives; semipermeable cross-linked poly(vinylbenzyltrimethyl ammonium chloride). The polymers are known in U.S. Pat. Nos. 3,845,770; 3,916,899; 4,783,337; and 4,160,020; and in the *Handbook of Common Polymers*, by Scott, J. R. and Roff, W. J., 1971, published by CRC Press, Cleveland, Ohio. In another manufacture, wall 12 of the dosage form optionally comprises from 0 weight percent (wt %) to 35 wt % of a member selected from the group consisting of a cellulose selected from the group consisting of hydroxyalkylcellulose, hydroxypropylalkylcellulose, hydroxymethylcellulose, hydroxypropylmethylcellulose, hydroxymethylcellulose, hydroxyethylcellulose, hydroxypropylethylcellulose, and hydroxypropylpentylcellulose said cellulose either having a 9,000 to 275,000 molecular weight; and 0 wt % to 30 wt % of a polyethylene glycol of 400 to 125,000 molecular weight. The total weight of all components comprising wall 12 is equal to 100 wt %.

Dosage form 10, in compartment 15, comprises an antiepileptic composition 16, which comprises at least one antiepileptic drug 17, represented by dot 17. Antiepileptic drug 17 comprises a member selected from the group consisting of valproic acid, pharmaceutically acceptable salts of valproic acid including sodium valproate, potassium valproate, calcium valproate; valproic acid and its amide valpromide; valproic acid esters, divalproex sodium, oligomers of a salt of valproic acid and valproic acid containing four moieties of the salt and the acid; a composition consisting of one to three moles of valproic acid and one to six moles of a pharmaceutically acceptable salt of valproic acid; prodrugs of valproic acid which biotransform to valproic acid in the plasma to the active antiepileptic form; three moles of valproic acid coordinated with calcium valproate; and compositions comprising two or more of the above drugs, such as a composition comprising valproic acid and sodium valproate, valproic acid and divatproex sodium, calcium valproate and valpromide. The amount of antiepileptic drug present in dosage form 10 is 10 nanograms to 750 milligrams.

A composition comprising antiepileptic drug 17 is provided by the invention by formulating a composition comprising drug 17 by blending drug 17 with a compositional forming means. The compositional forming means includes a member selected from the group consisting of a polymer possessing a repeating unit $-(O-CH_2CH_2)_n$ wherein n is 40,000 to 120,000 to provide a poly(alkylene oxide) having a molecular weight of 175,000 to 5,250,000; a maltodextrin polymer of the formula $(C_6H_{12}O_5)_n \cdot H_2O$ wherein n is a 50 to 62,000 and comprises a molecular weight of 9,000 to 10,000,000; and a carboxymethylcellulose polymer comprising a 10,000 to 5,000,000 molecular weight as represented by alkali carboxymethylcellulose, sodium carboxymethylcellulose, potassium carboxymethylcellulose, ammonium carboxymethylcellulose, sodium carboxymethyl-2-hydroxyethylcellulose, sodium carboxymethylcellulose, and sodium carboxymethyl-2-hydroxybutylmethylcellulose.

A composition comprising antiepileptic drug 17 is provided in another manufacture by formulating a composition comprising drug 17 blended with a lubricant. The lubricant is represented by magnesium stearate, calcium stearate, oleic acid, caprylic acid, stearic acid, magnesium isovalerate, calcium laurate, magnesium palmitate, behenic acid, glyceryl behenate, glyceryl stearate, sodium stearyl fumarate, potassium stearyl fumarate, and zinc stearate. The composition in an additional manufacture comprises antiepileptic drug 17 blended with a polymer selected from the group consisting of a hydroxyalkylcellulose polymer and a hydroxypropylalkylcellulose polymer wherein alkyl is 1 to 6 carbons.

The composition comprising antiepileptic drug 17 and the composition forming means that provides particles consisting of drug and the means is encapsulated or coated with a cellulose polymer. The cellulose polymer that encapsulates the particle comprises a member selected from a cellulose ether polymer consisting of a member selected from the group consisting of a hydroxyalkylcellulose and hydroxypropyl-alkylcellulose, hydroxypropylcellulose, hydroxypropylmethylcellulose, hydroxypropylethylcellulose, hydroxypropylisopropylcellulose, hydroxypropylpentylcellulose and hydroxypropyl-hexylcellulose comprising a 9,000 to 225,000 molecular weight. The cellulose polymer comprising the drug particle possesses a different molecular weight then the cellulose polymer comprising the encapsulation coat 18. The antiepileptic drug particles optionally can be compressed into a layer containing 0.1 wt % to 5 wt % of a lubricant 19 to assist in binding the particles into a layer. Lubricants useful for this purpose include the lubricants presented above. The polymers are known in U.S. Pat. Nos. 3,845,770; 4,200,098; and 4,783,337; and in *Handbook of Common Polmyers*, by Roff, W. J., and Scott, J. R., (1971) published by CRC Press, Cleveland, Ohio.

Compartment 15 comprises a push composition or displacement layer 22. Displacement layer 22 comprises an osmopolymer 23, represented by wavy line 23, which osmopolymer is noncross-linked or optionally cross-linked, and it possesses osmotic properties, such as the ability to imbibe an exterior fluid through a semipermeable wall, and exhibit an osmotic pressure gradient across a semipermeable wall against an exterior fluid. The osmopolymer imbibes biological fluid or water, swells or expands, retains a significant fraction of the imbibed fluid in the osmopolymer molecular structure, and through these molecular actions displace the drug composition from the dosage form. The osmopolymers, in one embodiment, are hydrogels that can swell or expand to a very high degree, usually exhibiting a 2 to 60 fold increase in volume. The osmopolymer can be of plant, animal or synthetic origin. Polymeric materials useful for the present purpose include poly(hydroxyalkyl methacrylate) having a molecular weight of from 5,000 to 5,000,000; poly(vinylpyrrolidone) having a molecular weight of from 10,000 to 4,500,000; anionic and cationic hydrogels; poly(electrolyte) complexes; poly(vinyl alcohol) having a low acetate residual; a swellable mixture of agar and carboxymethyl cellulose; a swellable composition comprising methyl cellulose mixed with a sparingly cross-linked agar; a water-swellable copolymer produced by a dispersion of finely divided copolymer of maleic anhydride with styrene, ethylene, propylene, or isobutylene; water swellable polymer of N-vinyl lactams; and the like.

Other gelable, fluid imbibing and retaining polymers useful for forming the hydrophilic, expandable push member include pectin having a molecular weight ranging from 30,000 to 300,000; polysaccharides such as agar, acacia, karaya, traga anth, algins and guar; Carbopol® acidic carboxy polymer and its salt derivatives; polyacrylamides; water-swellable indene maleic anhydride polymers; Goodrite® polyacrylic acid having a molecular weight of 80,000 to 200,000; Polyox® polyethylene oxide polymers having a molecular weight of 100,000 to 7,500,000; starch graft copolymers; Aqua-Keep® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000; and the like. In a preferred embodiment, the expandable member is formed from polymers and polymeric compositions that are thermoformable. Representative polymers possessing hydrophilic properties are known in U.S. Pat Nos. 3,865,108; 4,002,173; 4,207,893; 4,327,725, and in *Handbook of Common Polymers*; by Roff and Scott, published by Cleveland Rubber Company, Cleveland, Ohio.

Displacement layer 22 can comprise an osmotically effective compound also known as an osmotically effective solute that can be blended homogeneously or heterogeneously with the swellable polymer, to form a push member, the osmotically effective solutes are soluble in fluid imbibed into the dosage forms and they exhibit an osmotic pressure gradient across the semipermeable wall against an exterior fluid. Osmotically effective compounds are known also as osmagents. Osmotically effective osmagents useful for the present purpose include salts, esters, acids, carbohydrates, magnesium sulfate, magnesium chloride, sodium chloride, lithium chloride, potassium sulfate, potassium chloride, sodium sulfate, mannitol, sodium sulfite, potassium lactate, fructose, magnesium succinate, urea, sorbitol, inositol, sucrose, glucose, and the like. The osmotic pressure in atmospheres, A TM, of the osmagents suitable for the invention will be greater than zero ATM, generally from eight ATM up to 500 ATM, or higher. The displacement layer optionally comprises 0.5 wt % to 45 wt % of the osmagent.

Displacement layer 22 comprises a cellulose polymer, represented by the letter v and by the number 24. The cellulose polymer comprises a member selected from the group consisting of a hydroxyalkylcellulose, a hydroxypropylalkylcellulose, hydroxypropylcellulose, hydroxypropylethylcellulose, hydroxypropylmethylcellulose, hydroxypropylethylcellulose, hydroxyisopropyl-cellulose, hydroxypropylisopropylcellulose, hydroxypropylpentylcellulose, hydroxypropyl-butylcellulose, and hydroxyethylcellulose, comprising a 9,000 to 225,000 molecular weight. The concentration of the cellulose polymer 24 is 1 wt % to 30 wt %. Displacement layer 22 optionally comprises 0 wt % to 5 wt % of a lubricant illustrated by stearic acid, magnesium stearate, calcium oleate, potassium stearate, oleic acid, and caprylic acid. Displacement layer 22 comprises 0 wt % to 2 wt % of an antioxidant such as butylated hydroxyanisole, ascorbic acid, α-tocopherol, butylated hydroxytoluene, nordihydroquairetic acid and propylgallate.

Drawing FIG. 4 illustrates dosage form 10 comprising exit means 13. Expression "exit means" as used herein comprises means and methods suitable for releasing the pulsed dose from dosage form 10. The expression includes at least one passageway or orifice that passes through wall 12 for communicating with compartment 15. The expression "at least one passageway" includes aperture, orifice, bore, pore, porous element through which drug can migrate, a hollow fiber, capillary tube and the like. The expression includes also a is material that erodes or is leached from wall 12 in the fluid environment of use to produce at least one passageway in the dosage form. Representative materials suitable for forming at least one passageway, or a multiplicity of passageways include an erodible poly(glycolic) or poly(lactic) acid member in the wall, a gelatinous filament, leachable materials such as fluid removable pore forming polysaccharides, salts or oxides, and the like. A passageway or a plurality of passageways can be formed by leaching a material such as sorbitol, fructose, glucose, and sucrose, from the wall to produce a controlled release passageway. The passageway can have any shape, such as round, triangular, elliptical, and the like. The device can be constructed with one or more passageways in spaced apart relation on more than a single surface of a dosage form. Passageways and equipment for forming passageways are disclosed in U.S. Pat. Nos. 3,916,899; 4,063,064 and 4,088, 864. Passageways of controlled dimensions formed by leaching are disclosed in U.S. Pat. No. 4,200,098.

Drawing FIG. 3, illustrates dosage form 10 of FIG. 1 comprising body 11, wall 12, exit means 12, and exterior lamina 25 comprises a dosage unit amount of drug 17 for an initial pulsed dose of drug 13 to the environment of use, the gastrointestinal tract of a warm blooded animal. The initial pulse is the first dose of drug. Exterior lamina 25 comprises from about 0.1 to 99.9 weight percent (wt %) of a drug, and from 99.9 to 0.1 wt % of a pharmaceutically acceptable carrier for the drug, with the total wt % of all lamina 25 forming members equal to 100%. In a more preferred embodiment the initial pulse dose is from 10 to 80 wt % and from 90 to 20 wt % carrier. The carrier is a means for coating the drug onto the exterior surface of the wall, and the carrier comprising lamina 25 onto the exterior surface of wall 12. In the fluid environment of use, the carrier releases the drug thereby providing the initial or first pulsed dose of the drug to the environment of use. The carrier releases the initial pulsed dose in from greater than zero time up to 1 hour, and in a presently preferred pulsed dose time of from several minutes up to 30 minutes. Typical carrier means include a hydrophilic polymer, that are in a presently preferred embodiment a member selected form the group consisting of hydroxymethyl cellulose, hydroxyethyl cellulose, hydroxypropyl cellulose, hydroxypropyl methylcellulose and hydroxypropyl ethylcellulose.

Drawing FIG. 5 depicts a dosage form comprising an enteric coat 26 on its outer most surface of wall 12. The drawing FIG. 5 illustrates the enteric coat 26 on part of the exterior wall 12, but it is understood enteric coat 26 can cover the entire exterior surface of dosage form 12. The enteric materials suitable for forming enteric lamina 26 include: (a) enteric materials that are digestible by enzymes in the small intestine; (b) enteric materials containing an ionizable polyacid; and (c) enteric materials that are a long-chain polymer with an ionizable carboxyl group. Representative enteric materials include: (d) a member selected from the group of phthalates consisting essentially of cellulose acetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxy propyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, and polyvinyl acetate phthalate; (e) a member selected from the group consisting of keratin, keratin sandarac-tolu, salol, salol β-naphthyl benzoate and acetotannin, salol with balsam of Peru, salol with tolu, salol with gum mastic, salol and stearic acid, and salol and shellac; (f) a member selected from the group consisting of formalized protein, formalized gelatin, and formalized cross-linked gelatin and exchange resins; (g) a member selected from the group consisting of myristic acid-hydrogenated castor oil-cholesterol, stearic acid-mutton tallow, stearic acid-balsam of tolu, and stearic acid-castor oil; (h) a member selected from the group consisting of shellac, ammoniated shellac, ammoniated shellac-salol, shellac-wool fat, shellac-acetyl alcohol, shellac-steric acid-balsam of tolu, and shellac-n-butyl stearate; (i) a member selected from the group consisting of abletic acid, methyl abietate, benzoin, balsam of tolu, sandarac, mastic with tolu, and mastic with acetyl alcohol;(j) a member selected from the group consisting of cellulose acetate with shellac, starch acetate phthalate, polyvinyl acid phthalate, 2-ethoxy-5-(2-hydroxyethoxy-methyl)-cellulose phthalic acid, acid phthalates of carbohydrates, zein, alkyl resin unsaturated fatty acids-shellac, colophony and carboxymethylcellulose phthlate; and the like. The enteric materials are discussed in *Remington's Pharmaceutical Sciences*, 1985, 17th Ed., page 1637, published by Mack Publishing Co., Eaton, Pa.

PROVIDING THE DOSAGE FORM

The wall of the dosage form, the exterior instant release lamina and the enteric coat, can be formed in one step using the air suspension procedure. This procedure consists in suspending and tumbling drug bilayers in a current of air and a wall forming, or is outer instant release lamina composition, until in either operation the wall or the instant release lamina is applied to the bilayers. The air suspension procedure is well-suited for independently forming the wall of the pulsed lamina. The air suspension procedure is described in U.S. Pat. No. 2,799,241; in *J. Am. Pharm. Assoc.*, Vol. 48, pp. 451 to 450, 1959; and ibid, Vol. 49, pp. 82 to 84, 1960. The osmotic dosage systems can also be coated with the wall forming composition, or the lamina composition with Wurster® air suspension coater, using for example methylene dichloride-methanol cosolvent. The Aeromatic® air suspension coater can be used also employing a cosolvent. Other wall and laminating techniques such as pan coating can be used for providing the dosage form. In the pan coating system the wall forming, or the instant released lamina forming, compositions are deposited by successive spraying of the composition on the bilayers accompanied by tumbling in a rotating pan. A pan coater is used to produce a thicker wall or lamina. A larger volume of methanol can be used in a cosolvent to produce a thinner wall or lamina. Finally, the wall or lamina coated compartments are dried in a forced are oven at 50° C. for a week, or in a temperature and humidity controlled over for 24 hours at 50° C. and 50% or lower relative humidity, to free the dosage form of solvent. Generally, the wall formed by these techniques have a thickness of 2 to 20 mils with a presently preferred thickness of 4 to 10 mils. The exterior dose lamina generally will have a thickness of 0.5 to 15 mils, usually 0.5 to 7.5 mils.

Exemplary solvents suitable for manufacturing the wall or the lamina include inert inorganic and organic solvents that do not adversely harm the wall, the lamina and the final dosage system. The solvents broadly include a member selected from the group consisting of an alcohol, ketone, ester, ether, aliphatic hydrocarbon, halogenated solvents, cycloaliphatic solvents, aromatic, heterocyclic, aqueous solvents, and mixtures thereof.

The dosage form of the invention is manufactured by standard techniques. For example, in one manufacture the beneficial drug and other ingredients comprising the first layer facing the exit means are blended and pressed into a solid layer. The layer possesses dimensions that correspond to the internal dimensions of the area the layer is to occupy in the dosage form and it also possesses dimensions corresponding to the second layer for forming a contacting arrangement therewith. The drug and other ingredients can be blended also with a solvent and mixed into a solid or semisolid form by conventional methods such as ballmilling, calendering, stirring or rollmilling and then pressed into a preselected shape. Next, a layer of osmopolymer is placed in contact with the layer of drug in a like manner. The layering of the drug formulation and the osmopolymer hydrogel layer can be fabricated by conventional two-layer press techniques. The two contacted layers are first coated with a drug-free semipermeable wall and then with the optional enteric coat. The drug-free delayed composition can be applied by press coating, molding, spraying, dipping, and air suspension procedures. The air suspension and air tumbling procedure comprises in suspending and tumbling the pressed, contacting first and second layers in a current of air containing the wall forming composition until the first and second layers are surrounded by the semipermeable position.

In another manufacture, the dosage form is manufactured by the wet granulation technique. In the wet granulation technique the drug and the ingredients comprising the first layer are blended using an organic cosolvent, such as isopropyl alcohol-methylene dichloride 80/20 v/v (volume/volume) as the granulation fluid or anhydrous denatured ethanol. The ingredients forming the first layer are individually passed through a 20 mesh screen and then thoroughly blended in a mixer. Next, other ingredients comprising the first layer are dissolved in a portion of the granulation fluid described above. Then, the latter prepared wet blend is slowly added to the drug blend with continual mixing in the blender. The granulating fluid is added until a wet blend is produced, which wet mass blend is then forced through a 20 mesh screen onto oven trays. The blend is dried for 18 to 24 hours at 35° C. in a forced air oven. The dried granules are then sized with a 20 mesh screen. Next, magnesium stearate is added to the dry screened granule blend. The granulation is then put into milling jars and mixed on a jar mill for 5 to 10 minutes. The composition is pressed into a layer, for example in a Manesty® layer press. The speed of the press is set at 30 rpm and the maximum load set at 2 tons. The first layer is pressed against the composition forming the second displacement layer to form the bilayer tablets. The bilayer tablets are coated with a semipermeable wall.

Another manufacturing process that can be used for providing compartment 25 composition comprises blending the powdered ingredients in a fluid bed granulator. After the powdered ingredients are dry blended in the granulator, a granulating fluid, for example, a granulating polymer in water, is sprayed onto the powders. The polymer coated powders are than dried in the granulator. This process granulates all the ingredients present therein while adding the granulating fluid. After the granules are dried, a lubricant such as stearic acid or magnesium stearate is added to the granulator. The granules are then pressed in the manner described above.

DESCRIPTION OF EXAMPLES OF THE INVENTION

The following examples are merely illustrative of the present invention and they should not be considered as limiting the scope of the invention in any way, as these examples and other equivalents thereof will become more apparent to those versed in the art in the light of the present disclosure, the drawing figures and the accompanying claims.

EXAMPLE 1

6,825 grams of the sodium valproate and 300 grams of pharmaceutical acceptable poly(ethylene oxide), 5,000,000 molecular weight, is added to the bowl of Freund flo-coater fluid bed granulator. The microencapsulation process is computerized and atomized in cycles. The process is initiated by first fluidizing the dry drug and the polymer powder for 3 minutes and the blended is granules are microencapsulated with an aqueous hydroxypropylmethylcellulose solution. The polymer solution is prepared by dissolving 344 grams of hydroxypropylmethylcellulose comprising 11,200 molecular weight in 3,956 grams of water. The operating conditions are as follows: spray rate of 100 grams/min/nozzle (2 nozzles are used), inlet temperature 50° C.; outlet temperature 37° C. and process air flow of 800 ft³/minute. During the coating process, the filter bag is shaken for 10 seconds after every 15 seconds of solution spraying to remove any uncoated materials. A total of 2,704 grams of solution is applied. After solution spraying, the microencapsulated powder is dried in the granulator to reach a moisture content of 0.23%. The dried granulation is then passed through a 16 mesh screen. Next, a total of 53.1 grams of magnesium stearate is weighed out, screened through a 40 mesh screen, and blended into the granulation using a V-blender for 2 minutes. The granulation is stored in a tightly closed bag with desiccants.

Next the displacement-push composition is prepared as follows: first, 37,000.5 grams of sodium chloride, and 1,500.4 grams of red ferric oxide are separately screened through an 8 mesh screen using the quadrocomil. Then the screened ingredients plus 76,422 grams of pharmaceutical acceptable poly(ethylene oxide) comprising of 7,500,000 molecular weight, and 2,517 grams of hydroxypropylmethylcellulose comprising 11,200 molecular weight are dispensed into the bowl of the 120 kg Glatt fluid bed granulator. Next, the dry powders are air suspended and mixed for 3 minutes. To prepare the binder solution, first, 4,180 grams of hydroxypropylmethylcellulose comprising 11,200 molecular weight is dissolved in 48,560 grams of water, and 94 grams of butylated hydroxy toluene is dissolved in 589 grams of denatured ethanol. The two solutions are combined and mixed to form the final binder solution. The conditions monitored during the process are as follows: solution spray rate of 800 g/min (3 nozzles are used); inlet temperature 45° C.; outlet temperature 24° C., and process air flow of 3,000 ft³/min. The granulating process is computerized and automated in cycles. Each cycle contains 1.5 minutes of solution spraying followed by 10 seconds of bag shaking to remove any possible powder deposits. A total of 44,000 grams of solution is sprayed. After solution spraying, the granulated particles are dried in the granulator for 50 minutes at 21° C. to reach a moisture content of 0.29%. The granules are removed and sized through an 8 mesh screen. Then 278 grams of magnesium stearate, screened through a 16 mesh screen, is mixed into the granulation using a tumbler for 3 minutes at 8 rpm.

Next, the sodium valproate drug composition and the push composition are compressed using a Manesty Layer tablet press into bilayer cores of tablet shape as follows: first 696.6 mg of sodium valproate drug composition (550 mg of valproic acid equivalent) is added to a punch and lightly precompressed, then 421 mg of the push composition is added and the layers are pressed under a pressure head of 1.5 ton (3000 lbs) into a 0.75" length modified capsule (1.905 cm) contacting layered arrangement. The compression process is done in a humidity controlled environment. The relative humidity during the process is 35% RH (relative humidity) or lower. The compressed cores are stored in a tightly closed bag with desiccants.

The bilayered arrangements next are coated with a semipermeable wall. The wall-forming composition comprises 100% cellulose acetate having a 39.8% acetyl content. The polymer is dissolved in 100% acetone to make a 4% solid solution. The wall forming composition is sprayed at 26 grams/min onto and around the bilayer cores in a 12" Freund HCT-30 Hi-Coater until a dry weight of 90 mg/core is achieved.

Figure 7:
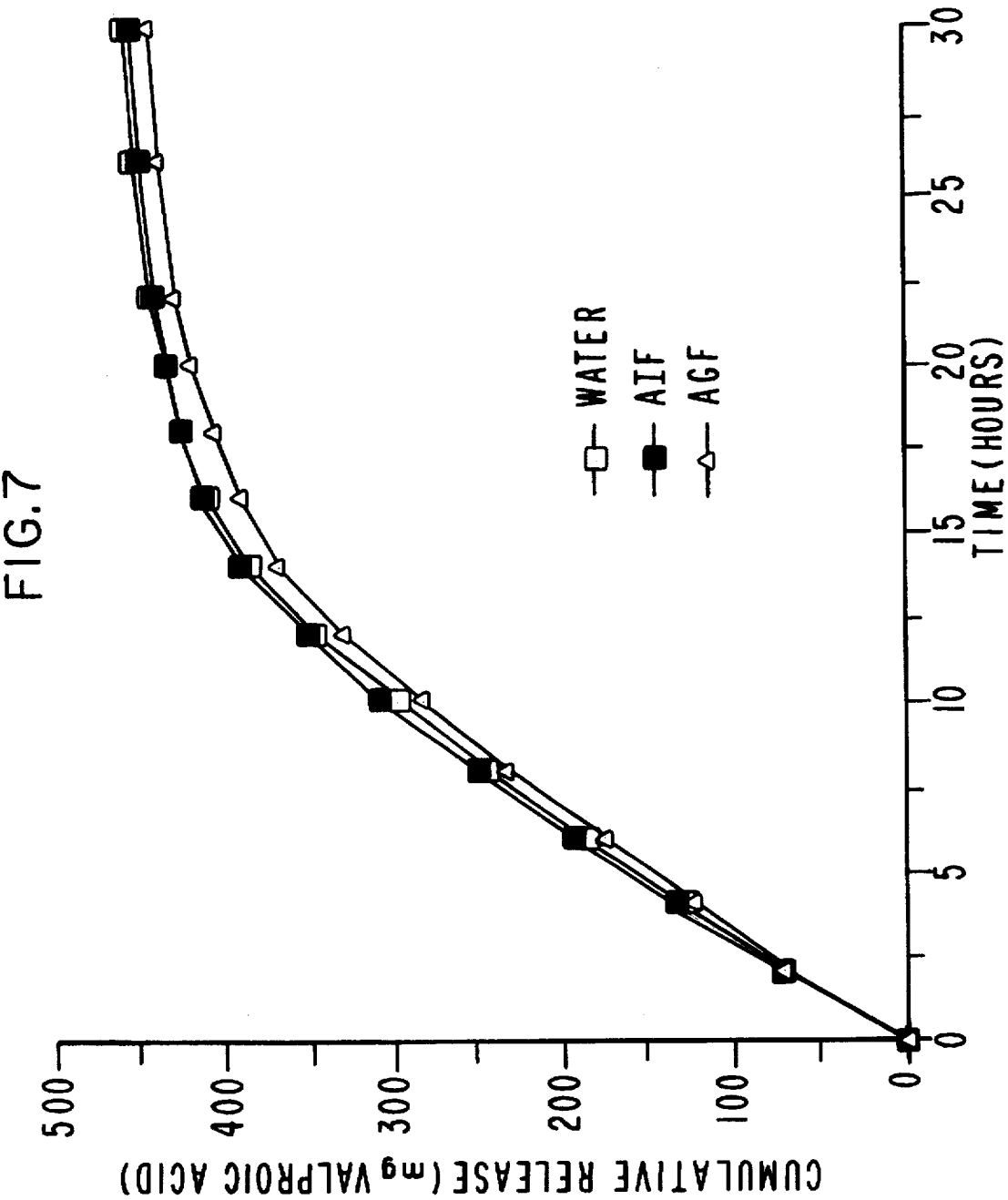
FIG. 7 depicts the cumulative amount released of valproic acid form a dosage form.

Next, one 10 mil (0.254 mm) exit passageway is mechanically drilled through the semipermeable wall to connect the drug layer with the exterior of the dosage system. The residual solvent is removed by first drying for 120 hours at 50° C. and 30% relative humidity, then the systems are dried for 2 hours at 50° C. to remove excess moisture. The drug dosage form produced by this process provides: 91 wt % sodium valproate, 4 wt % hydroxypropylmethylcellulose possessing a 11,200 molecular weight, 4 wt % poly(ethylene oxide) possessing 5,000,000 molecular weight and 1 wt % magnesium stearate in the drug layer. The push composition comprises 63.685 wt % poly(ethylene oxide) comprising a 7,500,000 molecular weight, 30 wt % sodium chloride, 4.99 wt % hydroxypropylmethylcellulose possessing a 11,200 molecular weight, 1 wt % red ferric oxide, 0.25 wt % magnesium stearate, and 0.075 wt % of butylated hydroxy toluene. The wall comprises 100 wt % cellulose acetate comprising a 39.8% acetyl content. The dosage form has one passageway, 10 mils (0.254 mm), and it has a sodium valproate release rate of 31.75 mg/hr (27.55 mg/hr of valproic acid equivalent) and an 18 hours $T_{90}$. The mean valproic acid equivalent released in 26 hours is depicted in drawing FIG. 6, and the cumulative amount of valproic acid equivalent released in 3 different pH medias is depicted in drawing FIG. 7. In FIG. 7, AIF denotes artificial intestinal fluid and AGF denotes artificial gastric fluid.

EXAMPLE 2

The procedure of Example 1 is followed to provide a system with enteric film wall protecting the dosage form in an acidic (gastric) environment. After the exit port drilling and drying, the dosage forms are coated with an enteric wall. The wall-forming composition comprises 98% cellulose acetate phthalate, and 2% triethyl citrate. The wall forming composition is dissolved in 100% acetone to make a 5% solid solution. The wall composition is sprayed onto and around the systems in a 12" Freund HCT-30 Hi-Coater at 26 grams/min. The processing conditions are as follows: inlet temperature 70° C.; outlet temperature 30° C.; and atomization air 20 psi. The dosage form is dried in the oven at 50° C. and 30% relative humidity for 120 hours to remove excess solvent. Next, the dosage form is dried for 2 hours in 50° C. to eliminate moisture.

Figure 8:
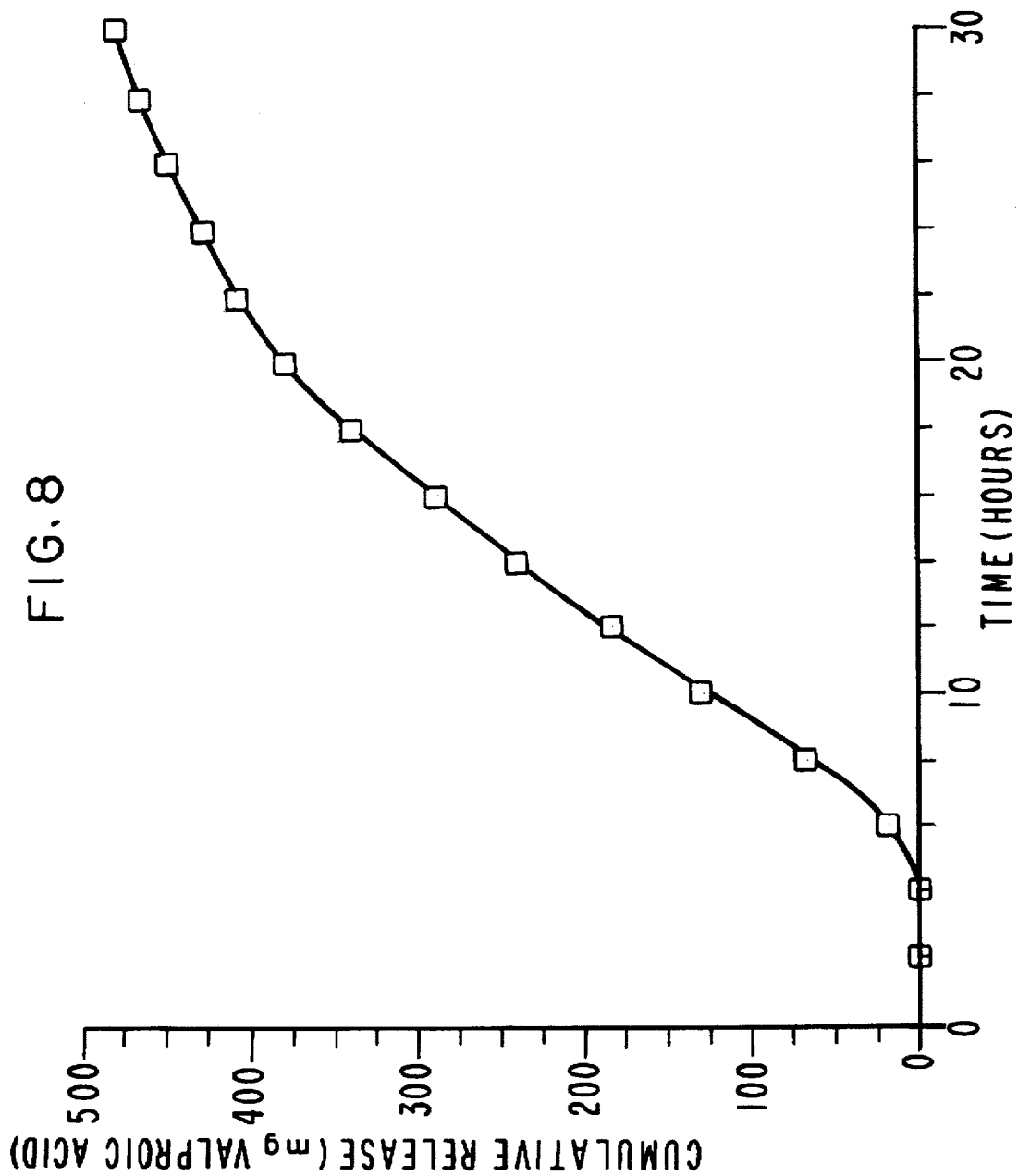
FIG. 8 depicts the cumulative amount released of valproic acid from a dosage form comprising an exterior enteric coat.

This dosage form consists of the same excipients as the dosage form described in Example 1 with an added enteric wall comprises 98 wt % cellulose acetate phthalate and 2 wt % triethyl citrate. The dosage form has no release rate in artificial astric fluid and has a sodium valproate release rate of 31.75, mg/hr (27.55 mg/hr of valproic acid equivalent) in artificial intestinal fluid. The cumulative amount of valproic acid equivalent released in 30 hours is depicted in drawing FIG. 8, where the dosage form is released in artificial gastric fluid in the first 4 hours and the remainder in artificial intestinal fluid.

EXAMPLE 3

Figure 9:
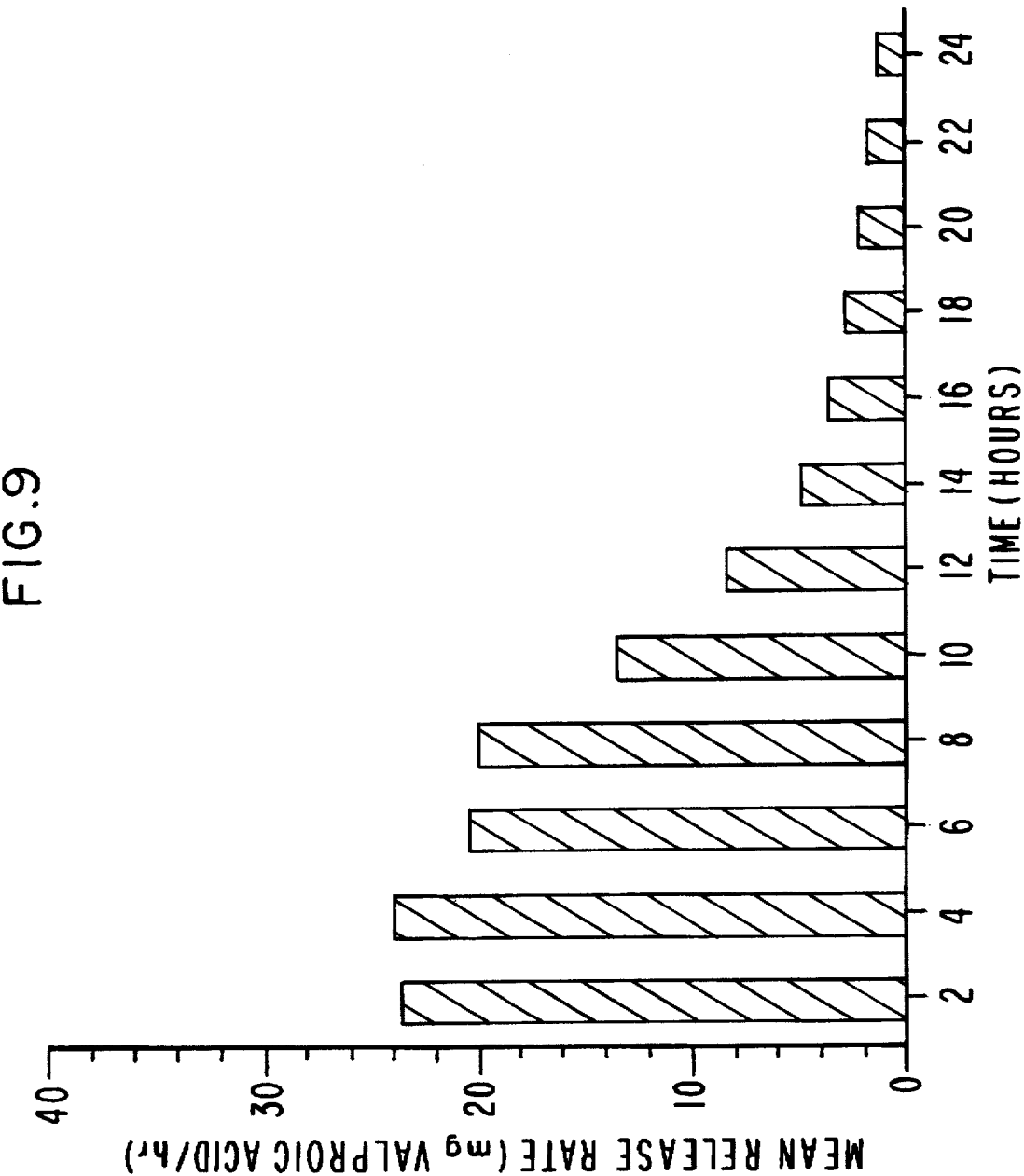
FIG. 9 depicts the release rate of valproic acid from a dosage form, at a lower dosage strength than FIG. 6.

The procedure of Example 1 and 2 are followed in this example to provide a dosage form comprising a total drug content of 250 mg of valproic acid equivalent. The dosage form contains 348.3 mg of the sodium valproate drug composition and 215 mg of the osmotic composition. The semipermeable coating process continues until 44 mg of wall-forming composition per dosage form is applied. The dosage form produced by the process contains the same wt % for both the drug and the osmotic composition as described in Example 1. The wall comprises 100 wt % cellulose acetate comprising 39.8% acetyl content. The dosage form comprises one passageway with a, 10 mils (0.254 mm) diameter and it has a sodium valproate release rate of 25.33 mg/hr (21.98 mg/hr of valproic acid equivalent), and a 13 hours $T_{90}$(time for the dosage form to release 90% of its drug content). The mean valproic acid equivalent release rate in 30 hours is depicted in drawing FIG. 9.

EXAMPLE 4

The procedures of the above examples are followed in this example, with the conditions as set forth, except that in this example the drug is a member selected from the group consisting of potassium valproate, calcium valproate, valpromide, valproic acid ester, divalproex sodium, and oligomer salt of valproic acid.

EXAMPLE 5

The procedure of the above examples are followed in this example, with the conditions as set forth, except that in this example the drug is a member selected from the group consisting of valproic acid and sodium valproate, valproic acid and divalproex sodium, sodium valproate and divalproex sodium, calcium valproate, and valpromide.

METHOD FOR DELIVERING AN ANTIEPILEPTIC DRUG

The invention pertains additionally to a method for delivering an antiepileptic drug to a patient in need of antiepileptic therapy. The method pertains, in one embodiment, to delivering an antiepileptic drug from a dosage form comprising 10 nanograms to 750 milligrams of the drug from a dosage form selected from a controlled-release and a sustained release dosage form. The method comprises delivering an antiepileptic drug to the gastrointestinal tract of a human in need of antiepileptic therapy, wherein the method comprises admitting orally into the gastrointestinal tract of the patient a dosage form comprising means for housing 10 nanograms to 750 milligrams of an antiepileptic drug, means for releasing the antiepileptic drug in a release pattern selected from the group consisting of controlled-release and sustained release over an extended period of time.

The invention pertains also to a method for delivering an antiepileptic drug to the gastrointestinal tract of a human in need of this therapy, wherein the method comprises the steps of: (A) admitting orally into the gastrointestinal tract of the human a dosage form comprising: (1) a non-toxic wall composition comprising means for imbibing an external aqueous fluid through the wall into the dosage form, which wall surrounds and defines; (2) an internal compartment; (3) an antiepileptic drug composition comprising an antiepileptic drug in the compartment comprising a dosage unit amount of said drug; (4) a push composition in the compartment for pushing the antiepileptic drug composition from the compartment; (5) at least one exit means in the wall for delivering the drug from the dosage form; (B) imbibing fluid through the wall into the compartment thereby causing the antiepileptic drug composition to form a deliverable dosage form and concomitantly causing the push composition to expand and push the antiepileptic drug composition through the exit means from the dosage form; and (C) deliver the therapeutic antiepileptic drug in a therapeutically effective amount at a controlled rate over an extended period of time to the patient in need of said therapy. The method also comprises dispensing a dose amount of said antiepileptic drug from an instant release exterior coat to the patient for providing instant antiepileptic therapy.

Inasmuch as the foregoing specification comprises preferred embodiments of the invention, it is understood that variations and modifications may be made herein, in accordance with the inventive principles disclosed, without departing from the scope of the invention.

We claim:

1. A dosage form for delivering a drug to an environment of use, wherein the dosage form comprises:

(a) a semipermeable wall that surrounds a therapeutic composition comprising 10 nanograms to 750 milligrams of an antiepileptic drug selected from the group consisting of valproic acid, valproic and salts, sodium valproate, potassium valproate, calcium valproate, valpromide, valproic ester, divalproex sodium, oligomer salt of valproic acid, prodrugs of valproic acid, and pharmaceutically acceptable derivations of valproic acid, and a member selected from the group consisting of a poly(alkylene oxide) and a carboxymethylcellulose, which composition is coated with a member selected from the group consisting of a hydroxyalkylcellulose and a hydroxypropylalkylcellulose;

(b) a displacement composition surrounded by the wall for pushing the therapeutic composition from the dosage form;

(c) en exit in the dosage form for delivering the therapeutic composition from the dosage form; and wherein the;

(d) antiepileptic drug is delivered from the dosage form in a therapeutically responsive dose over an extended period of time.

2. A dosage form for delivering a drug to an environment of use, wherein the dosage form comprises:

(a) a semipermeable wall that surrounds a therapeutic composition comprising 10 nanograms to 750 milligrams of a drug selected from the group consisting of one to three moles of valproic acid and one to six moles of a salt of valproic acid; an oligomer of valproic acid salt and valproic acid containing four moieties of the salt and the acid; three moles of valproic acid and calcium valproate; valproic acid and sodium valproate; valproic acid and divalproex sodium; and calcium valproate and valpromide; and a member selected from the group consisting of poly(alkylene oxide) and carboxymethylcellulose, which composition is coated by a member selected from the group consisting of a hydroxyalkylcellulose and hydroxypropylalkylcellulose;

(b) a displacement composition in the dosage form and surrounded by the wall, which displacement composition pushes the therapeutic composition from the dosage form;

(c) an exit in the dosage form for delivering the therapeutic composition from the dosage form; and wherein the;

(d) antiepileptic drug is delivered from the dosage form, in a therapeutically responsive dose over an extended time.

* * * * *